(12) United States Patent
Martin (10) Patent No.: US 6,943,885 B2
(45) Date of Patent: Sep. 13, 2005

(54) GAS CELL ADAPTED FOR CARBON DIOXIDE

(75) Inventor: Hans Göran Evald Martin, Delsbo (SE)

(73) Assignee: Senseair AB (SE)

( * ) Notice: Subject to any disclaimer, the term of this patent is extended or adjusted under 35 U.S.C. 154(b) by 293 days.

(21) Appl. No.: 10/258,164

(22) PCT Filed: Apr. 26, 2001

(86) PCT No.: PCT/SE01/00899
§ 371 (c)(1),
(2), (4) Date: Oct. 17, 2002

(87) PCT Pub. No.: WO01/81900
PCT Pub. Date: Nov. 1, 2001

(65) Prior Publication Data
US 2003/0136911 A1 Jul. 24, 2003

(30) Foreign Application Priority Data
Apr. 27, 2000 (SE) .............................. 0001564

(51) Int. Cl.$^7$ .............................................. G01N 21/00
(52) U.S. Cl. ........................ 356/437; 356/440; 250/343
(58) Field of Search ................................ 356/432–444, 356/244, 246, 335–343; 250/349, 343, 574–576

(56) References Cited

U.S. PATENT DOCUMENTS

| 4,245,910 A | 1/1981 | Källander | 356/338 |
|---|---|---|---|
| 4,557,603 A | 12/1985 | Oehler et al. | 356/418 |
| 4,657,397 A * | 4/1987 | Oehler et al. | 356/414 |
| 5,009,493 A | 4/1991 | Koch et al. | 350/619 |
| 5,170,064 A | 12/1992 | Howe | 250/573 |
| 6,120,166 A * | 9/2000 | Price | 362/302 |
| 2003/0058439 A1 * | 3/2003 | Martin | 356/246 |

FOREIGN PATENT DOCUMENTS

| WO | 97/10460 | 3/1997 |
|---|---|---|
| WO | 98/09152 | 3/1998 |

* cited by examiner

Primary Examiner—Hoa Q. Pham
(74) Attorney, Agent, or Firm—Ostrolenk, Faber, Gerb & Soffen, LLP (57) ABSTRACT

The invention relates to a gas cell (1) adapted for carbon dioxide and including a cavity (10) which is adapted for a chosen gas volume, a light s source (11) and a light-bundle receiving unit (12). The light source (11) is placed in a focal point (F) associated with a partially elliptical mirror surface (13) forming a reflector for the light source (11) and a first defining surface of the cavity (10). Two other cavity-defining surfaces are comprised of gas-conducting surfaces (14a, 14b) orientated from the end-parts (13a', 13b') of the mirror surfaces (13a, 13b). The light-bundle receiving unit (12) is placed in a second focal point (F') associated with the partially elliptical mirror surfaces (13a, 13b).

16 Claims, 4 Drawing Sheets

GAS CELL ADAPTED FOR CARBON DIOXIDE

FIELD OF INVENTION

The present invention relates primarily to a gas cell and more particularly to a gas cell adapted for carbon dioxide and including a cavity for receiving a volume of gas to be assayed, a light source and a light-beam or light-bundle receiving unit, also referred to as a detector.

By a gas cell adapted for carbon dioxide is meant a gas cell in which a light source generates bundles of light rays, where the light bundles are influenced by the gas present in the cavity by absorption spectrometry during passage of the light bundles along an optical measuring path extremity in the cavity, such that a detector is able to determine the presence of carbon dioxide and/or the instant concentration of carbon dioxide in a gas mixture.

The carbon dioxide-adapted gas cell includes a cavity-adapted light source placed at a focal point for a partially elliptical mirror surface that forms a first cavity defining surface.

More particularly, the present invention relates to a miniaturised gas cell which enables the presence of carbon dioxide and/or the concentration of carbon dioxide in a small gas sample enclosed in a cavity of small volume to be determined by absorption spectrometry.

The invention has been developed to enable the carbon dioxide content of a small volume of exhalation gas to be determined at the end phase of the exhalation cycle (the measurement value) and is intended to find suitable application in postoperative monitoring processes.

DESCRIPTION OF THE BACKGROUND ART

It has long been known in conjunction with absorption spectrometry to use electromagnetic waves, particularly light beams or bundles (groups) of light rays, that have a frequency in the infrared range, and to allow said beams or light bundles to pass along an optical measuring path extremity and to arrange for these light beams to be received by a detector.

In the case of gas sensors that are based on absorption technology, the light beams shall be allowed to pass through a gas sample enclosed in the cavity of a gas cell, in which a given volume of a chosen gas will result in frequency-dependent absorption of the light rays.

In this respect, a detector is adapted to detect the frequency spectrum of the light beams in respect of a gas or gas concentration currently in the cavity, and the gas or gas concentration can be determined by evaluating the intensity of the detected light beams in relation to a chosen intensity of the incident light beams and the absorption coefficient of the gas present in the cavity with respect to the light concerned, or the electromagnetic wavelength.

The cavity in the gas cell is normally formed by at least one first and one second part whose internal surfaces have each been treated to provide surfaces that will strongly reflect the incoming light beams.

This treatment will normally comprise coating said inner surface with one or more metal layers, wherewith the metal layer last applied forms the reflective surface.

The metal and the method chosen for this coating process will depend on the desired optical quality of the surfaces and for which optical wavelength or wavelengths the surfaces shall provide the reflection intended. The material in the body of the gas cell shall also be taken into consideration.

By way of example of the present standpoint of techniques can be mentioned the gas sensors illustrated and described in International Patent Application PCT/SE96/01448, Publication No. WO97/10460, and International Patent Application PCT/SE97/01366, Publication No. WO98/09152.

The contents of the following patent publications can also be considered to belong to the present state of the art as related to the technical field of the present invention.

D1: U.S. Pat. No. 5,170,064

This publication illustrates and describes a gas analyzer and in particular an analyzer for determining the instant, or current, concentrations of one or more gases.

The analyzer comprises a body that includes a cavity which includes an elliptically shaped light-reflective surface.

This surface is designed to define two focal points.

In this regard, there is provided a chamber (2) for enclosing the gas volume to be measured or assayed, said chamber (2) having a chosen height dimension, and a chamber (4) which is intended to enclose an inert gas and which has a height commensurate with half the height of the chamber (2).

There is also included a further chamber (3) which is used to enclose a reference gas, wherein the height of this further chamber is equal to the height of the chamber (4).

It is also proposed in this prior publication that the radiation source (24) shall be placed at a first focal point (11), while two radiation detectors (26, 27) shall be placed at a second focal point (12).

Each of the radiation detectors (26, 27) is allocated its respective chamber, where one chamber is intended for the inert gas and the other chamber is intended for the gas used as a reference.

The analyzer also includes partition walls (17, 18) or windows that form a gas-tight connection between an upper wall part (14a) and a lower wall part (14b), and also a partition wall (16) that functions to separate the chambers (3, 4) one from the other.

The chamber (2) includes holes (15) that allow the gas to be assayed or measured to pass through the chamber (2).

The partition walls (17, 18) are placed significantly closer to the focal points (12) than to the focal point (11), so as to create a measuring chamber (12) of relatively large measuring volume.

D2: U.S. Pat. No. 4,245,910

This publication illustrates and describes an arrangement adapted to function as a dust indicator which enables the presence in the gas of small particles to be detected, these particles either being in a solid or a liquid state.

In this case, concentrated, essentially parallel, light beams (1) of chosen wavelength are directed through the measuring chamber (2) that encloses the gas to be analyzed.

The light beams are enclosed by an inwardly directed, reflecting elliptical and cylindrical reflector (4) such that the light beams will coincide with a focal axis (B1).

A light-sensitive detector (6) is disposed at the other focal axis (B2) of said reflector.

The arrangement also includes a part (7) which has been designed to allow the gas being analyzed to pass into the measuring chamber, wherewith said part can be given any desired form, and wherein the detector (6) can be disposed in an opening in said wall part.

It is proposed especially that the inner surface of said part (7) shall be non-reflective.

SUMMARY OF THE PRESENT INVENTION

Technical Problems

When taking into consideration the technical deliberations that a person skilled in this particular art must make in order to provide a solution to one or more technical problems that he/she encounters, it will be seen that it is necessary initially to realize the measures and/or the sequence of measures that must be undertaken to this end on the one hand, and on the other hand to realize which means is/are required to solve one or more said problems. On this basis, it will be evident that the technical problems listed below are highly relevant to the development of the present invention.

When considering the present state of the art as described above, it will be seen that a technical problem resides in providing a gas cell adapted for carbon dioxide and including a cavity adapted for a chosen small gas volume, and including a light source and a light-bundle receiving unit which are so constructed as to be useful beneficially in respect of very small gas volumes, for instance volumes of less than 100 ml.

It will also be seen that a technical problem resides in the creation of conditions, with the aid of simple means, that will enable the concentration of carbon dioxide in very small available gas volumes to be determined reliably, and therefore enable the concentration of carbon dioxide in the expiration air of children and small animals, such as rats, to be determined.

It will also be seen that a technical problem resides in the creation of conditions that will also enable the carbon dioxide content to be determined in the final phase of the expiration cycle of new-born babies.

Moreover, in the case of very small available gas volumes, a technical problem resides in deflecting for determining carbon dioxide contents such a small proportion of said gas as to allow said small proportion to be released freely to the ambient air and therewith reduce the risk of infection that the return of a gas portion used in the process would otherwise imply.

Another technical problem is one of realizing the significance of and the advantages associated with the use of a short optical measuring path extremity within a cavity of limited measurements, so as to create conditions that will enable said measuring extremity to be given a length sufficient to enable a detector to determine the concentration of carbon dioxide in the gas.

In the case of a gas cell of the aforedescribed kind intended for determining the carbon dioxide content of a gas, it will be seen that a technical problem resides in the significance of realizing that the light source may be placed at a focal point of a partially elliptical reflective mirror surface or mirror surfaces, and to allow said mirror surfaces to form a first cavity defining surface, while one or two other cavity defining surfaces shall be comprised of gas-conducting surfaces oriented from the end-parts of said mirror surfaces towards the detector.

Another technical problem is one of realizing the significance of and the advantages afforded by allowing the unit or detector receiving the light bundles to be placed at a second focal point associated with the partially elliptical mirror surface.

Another technical problem is one of realizing the significance of and the advantages afforded by allowing the second defining surfaces to be adapted for direct connection with the end-parts of said mirror surfaces.

Yet another technical problem is one of realizing the significance of and the advantages afforded by allowing the ratio between a major axis and a minor axis in respect of the elliptical shape of the mirror surfaces to lie between 4:1 and 2:1, such as about 2.5:1.

Yet another technical problem is one of being able to realize the significance of and the advantages afforded by allowing the gas-cell cavity to be delimited by mutually parallel planar surfaces.

Another technical problem is one of realizing the significance of allowing the distance between said planar surfaces to equal approximately the chosen length of an incandescent filament included in the light source.

Another technical problem is one of realizing the significance of allowing a cavity-associated first plate to include a recess that functions as a light-source holder, and that the same plate may include a recess that functions as a holder for the light-bundle receiving unit, and to form said cavity in the plate between said holders.

Another technical problem is one of realizing the significance of enabling a sheet to be applied to said plate, and to provide said sheet with a gas-delivery opening and a gas-discharge opening.

Another technical problem is one of realizing the significance of and the advantages afforded by holding together said first plate and one or more sheets with the aid of a second and a third plate, and by providing said second plate with respective gas-delivery and gas-discharge connections.

A technical problem also resides in realizing the significance of and the advantages afforded by allowing an optical measuring path extremity of from 4 to 20 mm to be obtained via the elliptical mirror surface between the light source and the unit receiving the light bundles, in accordance with requirements.

Another technical problem resides in providing a gas cell adapted for carbon dioxide where the cavity has a small volume, for instance a volume of from 30 $\mu l$ to 100 $\mu l$, such as 40–60 $\mu l$ (microliters).

Another technical problem is one of realizing the significance of and the advantages gained by adapting the speed of the carbon dioxide gas to be measured in the cavity so as to enable a gas exchange of from 1–50 times per second to be achieved.

Another technical problem is one of realizing the significance of varying the speed of the gas in accordance with the application concerned, and therewith choose a speed which will enable the gas to be changed from 5 to 10 times per second.

In addition, it will be seen that a technical problem is one of realizing the significance of and the advantages afforded by building on a basic concept that leads towards reducing the measuring volume to the greatest possible extent and therewith enable said measuring volume to be quickly exchanged and therewith obtain short measuring cycles although with the use of a sufficiently long measurement path extremity and with the use of high light intensity, by utilizing not only light that is reflected by the elliptical reflective surfaces but also light that is reflected by the mutually parallel, upper and lower reflective surfaces that delimit the volume of the measurement chamber.

It will also be seen that a technical problem is one of realizing the significance of and the advantages afforded by adapting the distance between the parallel reflective surfaces to correspond or at least only slightly exceed the total length of an incandescent filament used, this length being approximately 1.5 mm by way of example in the case of present technology.

Solution

The present invention builds on a gas cell which is adapted for carbon dioxide and which has a cavity, adapted for a chosen small gas volume, a light source, and a unit or detector for receiving the light bundles, wherein the light source is placed in a focal point associated with one or more partially elliptical mirror surfaces forming a first cavity defining surface.

In the case of a gas cell of this kind adapted for carbon dioxide, it is proposed in accordance with the invention that two further cavity defining surfaces shall be comprised of gas conducting surfaces oriented from the end-parts of the mirror surfaces, and that the light-bundle receiving unit shall be placed at a second focal point associated with the partially elliptical mirror surfaces.

With the intention of solving one or more of the aforesaid technical problems, it is proposed in accordance with the present invention that the cavity is delimited by parallel planar surfaces, where the distance between said planar surfaces shall correspond to the length of the incandescent filament in the light source.

By way of embodiments that lie within the scope of the inventive concept, it is proposed that these further defining or delimiting surfaces are adapted for direct connection with the end-parts of said mirror surfaces.

It is also proposed in accordance with the invention that the ratio of the major axis to the minor axis of the elliptical mirror surfaces lies within the range of 4:1 to 2:1, such as about 2.5:1.

It is also proposed in accordance with the invention that a first cavity-associated plate shall include a first recess which functions as a light-source holder, and that the same plate includes a second recess which functions as a holder for the unit or detector receiving said light bundles, and that the cavity is formed between these holders.

It is also proposed in accordance with the invention that a sheet which includes a gas delivery inlet and a gas discharge outlet is applied to said plate.

Is also proposed that a second and a third plate are provided for holding together said first plate and one or more sheets, where said second plate is provided with respective gas-supply and gas-discharge connections.

It is also proposed that an optical measuring path extremity, via the elliptical mirror surfaces between the light source and the unit or detector receiving the light bundles, has a length of 4 to 20 mm.

It is also proposed that the volume of the cavity will preferably measure from 30 $\mu l$ to 100 $\mu l$, such as between 40 and 60 $\mu l$.

The velocity of the gas containing carbon dioxide and intended for analysis within the cavity can be adapted to enable the gas to be exchanged or replaced from 1 to 50 times per second.

On certain occasions, this speed shall be adapted to enable gas exchanges of from 5 to 10 times per second to be achieved.

Advantages

Those advantages primarily associated with a gas cell adapted for carbon dioxide and having features significant of the present invention reside in the provision of conditions for obtaining a cavity of very small volume while still providing an optical measuring path extremity of sufficient length to enable the gas cell to be used for determining the presence of carbon dioxide and/or determining the concentration of carbon dioxide in a small volume of gas mixture present in said cavity.

The invention enables the concentration of carbon dioxide in the exhalation air of small animals, such as rats, and small children, such as new-born babies, to be evaluated in such small volumes that render it unnecessary to return the gas volume used for measuring purposes.

The invention enables the carbon dioxide content (about 5% by volume) of the exhalation air to be measured solely at the terminal phase of the exhalation cycle.

BRIEF DESCRIPTION OF THE DRAWINGS

A gas cell adapted for carbon dioxide and having features significant of the present invention will now be described in more detail by way of example and with reference to the accompanying drawings, in which.

DESCRIPTION OF AN EMBODIMENT AT PRESENT PREFERRED

Figure 1:
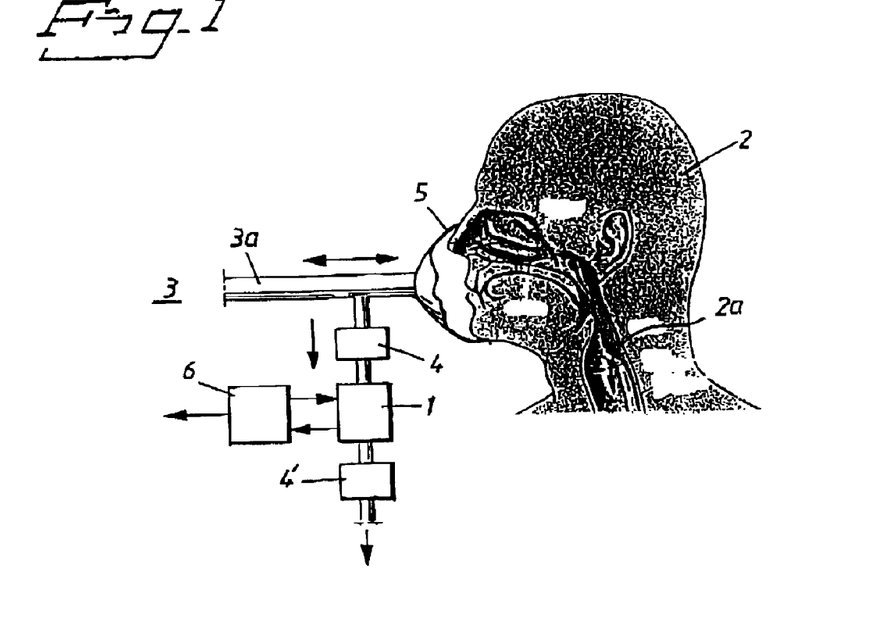
FIG. 1 illustrates a gas cell adapted for carbon dioxide connected to a respiratory system designed for small children.

FIG. 1 thus illustrates schematically a gas cell 1 which is adapted for carbon dioxide and which is used to determine the concentration of carbon dioxide in the expiration air of a child 2.

The expiration air shall thus pass the air passageways 2a and through a pipe system 3a to a respiratory device 3 (not shown).

A breathing mask 5 is connected to the pipe system or a hose 3a.

Figure 2:
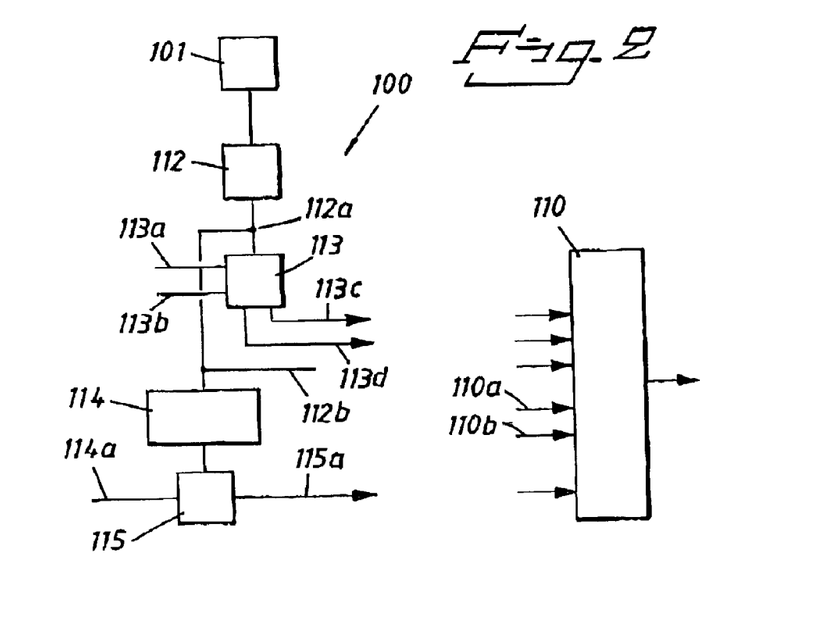
FIG. 2 is a block diagram that illustrates a carbon dioxide gas detector adapted for determining the instant concentration of carbon dioxide and/or the carbon dioxide concentration formed by mean values.

The gas cell 1 may be integrated with a central processing unit 6, in the way shown in FIG. 2.

A one-way valve shown in FIG. 1 may conveniently be replaced with a pump 4' that sucks the gas volume to be analysed from the pipe system 3a and out into the free atmosphere, as shown by the arrows.

The circuit arrangement shown in FIG. 2 will be described in more detail hereinafter.

The system can be constructed to determine solely the carbon dioxide content of the exhalation air in the final phase of the exhalation cycle.

Referring to FIGS. 3, 4, 5 and 6, there is shown a gas cell 1 which is adapted to determine the carbon dioxide concentration of a gas, said cell comprising a cavity 10, which is adapted to accommodate a chosen gas volume, a light source 11, and a unit or detector 12 for receiving the bundles or groups of light rays 11a, 11a' and 11b, 11b' respectively.

Figure 3:
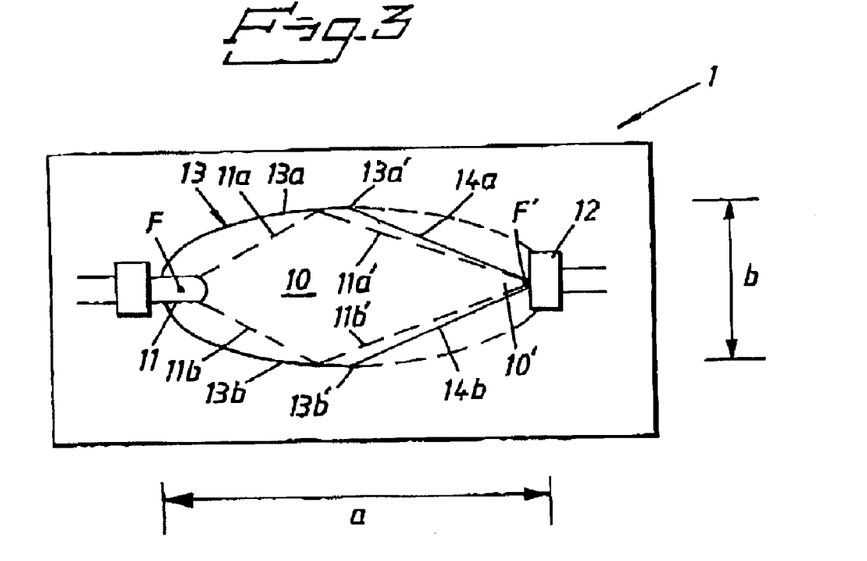
FIG. 3 is a schematic plan view of a gas cell adapted for carbon dioxide.

The light source 11 is placed with its incandescent filament at a focal point F of a partially elliptical mirror surface 13, which in the illustrated case comprises two parts, i.e. an upper part 13a and a lower part 13b as seen in the figure.

More specifically, the partially elliptical mirror surfaces 13a, 13b are intended to form a reflector in the form of a semi-ellipse in the plane according to FIG. 3.

The elliptical mirror surfaces 13a, 13b forming said reflector form together a first defining or delimiting surface of the cavity 10.

Two further cavity-defining surfaces 14a, 14b are comprised of surfaces 14a, 14b which converge mutually from the end-parts 13a, 13b of the mirror surfaces 13a, 13b.

These surfaces 14a, 14b are primarily intended to serve as gas-flow conducting surfaces, and the convergent form shown in FIG. 3 is adapted for a minimum volume of the cavity 10.

If a cavity of greater volume can be accepted, there is nothing to prevent the surfaces 14a, 14b from being formed in accordance with the elliptical shape shown in broken lines in FIG. 3, or given a still greater size.

These surfaces will preferably not have light-reflective properties, but will have, instead, light-absorbent properties; said surfaces will definitely not have light-reflective properties in certain applications.

The unit 12 receiving the light bundles is placed at a second focal point F' associated with the extension of the partially elliptical mirror surface 13 into a complete elliptical shape.

The second defining surfaces 14a, 14b are adapted more particularly for direct connection to or continuous connection with the end-part 13a', 13b' of the mirror surfaces.

The ratio between a major axis "a" and a minor axis "b" of the allocated elliptical shape 13 may, theoretically, be very large, although with respect to the outer dimensions of the light source 11 and the length of the incandescent filament together with the limitation resulting from the beneficial preference that the detector 12 shall solely receive light rays that are incident within the angular range ±30°, it means in practice that the ratio "a/b" including the elliptical shape of the mirror surfaces 13a, 13b shall be chosen to lie within the range of 4:1 to 2:1, such as about 2.5:1.

Figure 5:
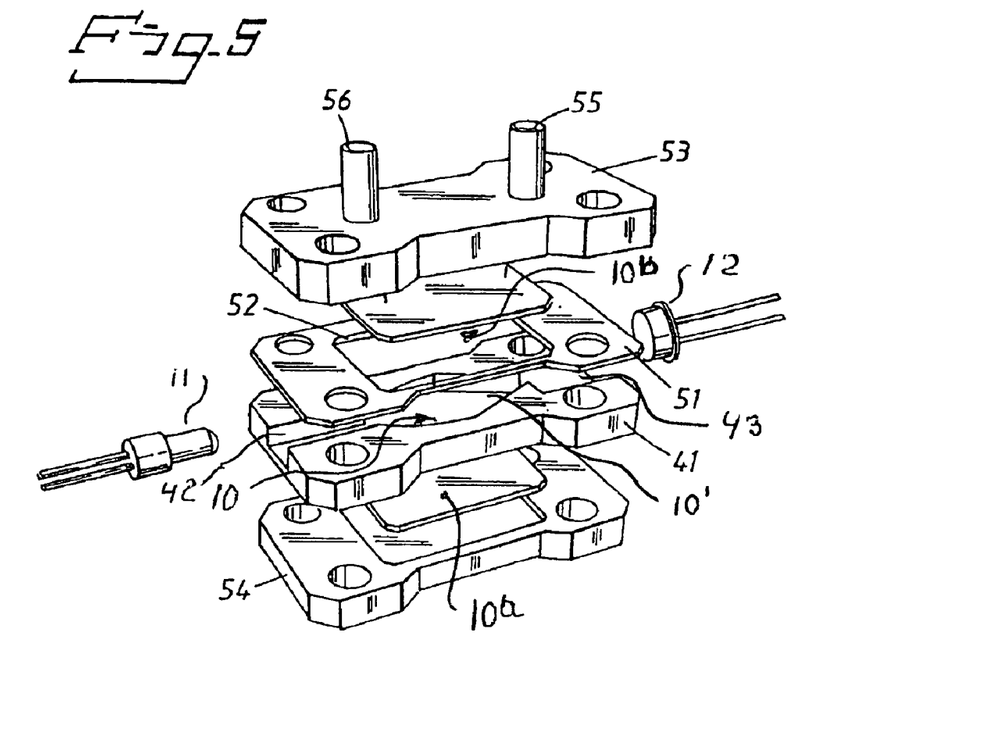
FIG. 5 is an exploded view of a prototype construction of a gas cell adapted for carbon dioxide.

In the FIG. 5 illustration, the cavity 10 is defined by parallel planar surfaces 10a and 10b, where the distance between said planar surfaces is chosen to correspond to the length of the incandescent filament G in the light source. This length may be in the order of about 1.5 mm.

The incandescent filament shall be orientated centrally in the focal point F and perpendicular to the plane shown in FIG. 3.

It is particularly proposed in respect of a prototype that a first plate 41 is provided with a first recess 42 that functions as a holder for the light source 11, that the same plate 41 is provided with a second recess 43 that serves as a holder for the unit 12 receiving the light bundle, and that the cavity is formed between said holder so that the incandescent filament will be placed centrally at focal point F and the detector 12 will be placed centrally at focal point F, to which focal points the delivery and discharge of the gas are also directed.

With reference to FIG. 5, the illustrated prototype includes a sheet 51 which can be applied to the plate 41 and which includes a respective gas-supply 52 and gas-discharge recess or opening.

A second plate 53 and a third plate 54 are arranged to hold together said first plate 41 and one or more sheets 51, and the second plate 53 is provided with gas-supply and gas-discharge connections 55 and 56 respectively. The exploded view of FIG. 5 is intended to illustrate that in respect of a gas cell which consists solely of two parts, some chosen parts in FIG. 5 can be integrated and assigned to one part or to a function block, and other parts can be integrated and assigned to the second part or a function block.

An optical measuring path extremity between the light source 11 and the unit 12 receiving the light bundles, via respective elliptical mirror surfaces 13a and 13b, will have a length of from 4 to 20 mm.

An optical measurement path extremity is illustrated via the directly-emitted light bundle 11a having been reflected by the mirror surface 13a as a light bundle 11a; a further measurement path extremity associated with the light bundles 11b, 11b' is also shown.

The dimensions indicated in FIGS. 3–6 are therefore significantly enlarged.

The cavity 10 shall therewith have a volumetric capacity of from 30 $\mu$l to 100 $\mu$l, such as between 40 and 60 $\mu$l (microliters).

The speed at which the gas to be analysed with respect to its carbon dioxide content travels in the cavity 10 is adapted to enable the gas to be replaced or exchanged from 1 to 50 times per second.

In certain cases, the gas speed may be adapted to allow the gas to be replaced or exchanged from 5 to 10 times per second.

This can be effected by controlling the pump 4' in FIG. 1.

Figure 6:
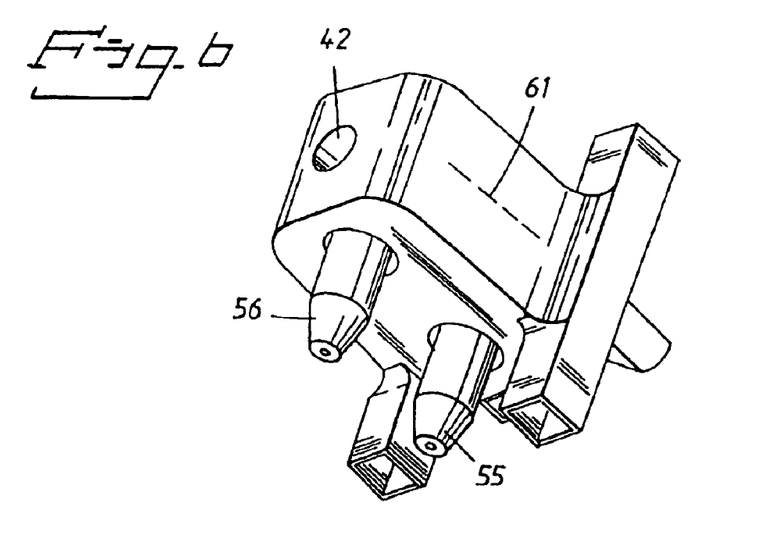
FIG. 6 is a perspective view of a gas cell adapted for carbon dioxide, and shows the cell in an assembled and integrated state and adapted for mounting on a printed circuit board or card.

FIG. 6 is a perspective view of a two-part gas cell adapted for carbon dioxide measurement. The cell is divided along the line 61 and includes connections 55, 56 and an opening 42 for the light source 11. The gas cell is also provided with connecting lines for supplying energy to the light source and for evaluating signals from the light-bundle receiving unit.

Included in the block diagram shown in FIG. 2 is a sensor unit 100, which can be considered as an integration of the gas cell 1 and the central processing unit 6 shown in FIG. 1.

This sensor may conveniently consist of a construction described and illustrated more clearly in International Patent Application PCT/SE96/01448 (SE95 04020-0) or International Patent Application PCT/SE97/01366 (SE96 03109-1) based on spectral analysis of a gas mixture present in the cavity of a measuring cell.

Raw data delivered by the sensor 101 is subjected to an adapted signal processing procedure in a circuit 112, for instance. This signal processing procedure may include dynamic filtration, temperature adjustment or temperature compensation, linearisation and/or calibration.

A signal representative of the instant value of the measured $CO_2$ concentration, such as the end-tidal values is delivered on a line 112a.

This signal is delivered to a circuit 113 which, via a control signal on a line 113a, can indicate a set threshold value for a chosen ceiling value or an upper value, and a control signal on a line 113b can indicate a set threshold value for a chosen lower value.

Thus, the instant values are compared in the circuit 113 and when said instant values exceed a set value, an emergency alarm unit is activated via the line 113c, and when the instant values fall below a set value, an emergency alarm unit is activated via the line 113d.

The values relating to carbon dioxide concentrations and/or other patient-related values of signals on the line 112a are processed in a circuit 114 and said value compared in a circuit 115 with a set threshold value for the breathing frequency, via an adapted signal on a line 114a.

The signals, in the form of alarm flags on the lines 113c, 113d and 115a, are coordinated with instant $CO_2$ concentrations on the line 112b in a transmitter 110, to which measurement values of other gases carried on lines 110a, 110b may also be applied.

The transmitter 110 is now able to effect wireless transmission of the information obtained to a receiver in the central unit, in which a comparison can be made of the flag status indicated by several connectable and connected sensor units 100.

The transmitter 110 may be provided with alarm circuits for emergency-related alarm signals, acoustic and/or optical signals, and an alarm circuit for an environment-related alarm signal, an acoustic and/or optical signal.

It has earlier been mentioned that the detector 12 is adapted primarily to receive light beams that fall within the angular range of ±30°.

In certain applications, it may be appropriate to give the surfaces 14a, 14b a light-absorbent structure, such as a microstructure. Similarly, the surface parts 10' may be given a light-absorbent structure to prevent the ingress of disturbing light externally of this angular area.

The supply and discharge of gas has been illustrated adjacent respective focusing points F and F' in FIG. 3.

However, there is nothing to prevent the reflector parts 13a, 13b from being divided into sections with gas supply and/or gas discharge points disposed therebetween, and to divide the surfaces 14a, 14b into sections with gas inlet and/or gas outlet points disposed therebetween.

The bottom surface 10a and a ceiling surface may be perforated to allow the passage of gas at right angles to the plane of FIG. 3.

Figure 4:
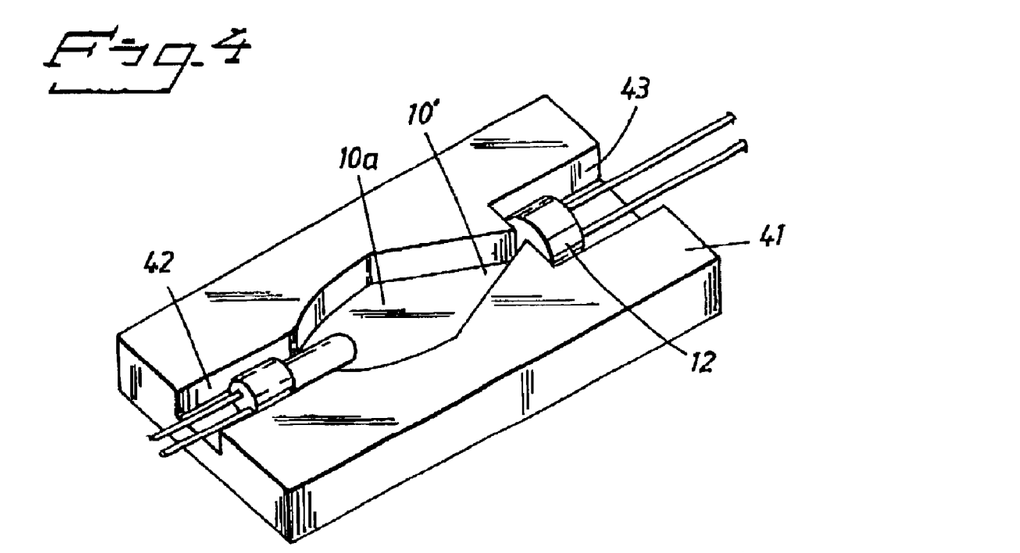
FIG. 4 is a perspective view of the gas cell shown in FIG. 3.
Figure 7:
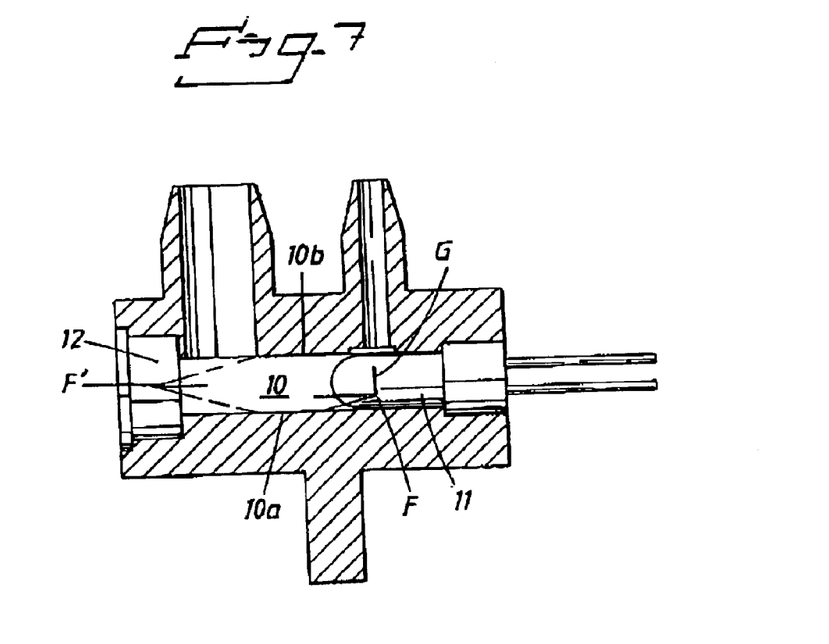
FIG. 7 is a sectioned view of the gas cell shown in FIGS. 4, 5 and 6 including incandescent filament and detector.

FIG. 7 is a sectioned view of a gas cell according to FIGS. 4, 5 and 6, and shows the cavity 10, an incandescent filament 11 and a detector 12.

This illustrated embodiment includes a bottom surface 10a and a ceiling surface 10b, said surfaces being planar and mutually parallel and functioning to reflect incident light.

The used expression "parallel" shall also be understood to include mutually opposing surfaces that may have a slightly other form than parallel.

It will be seen from FIG. 7 that the incandescent filament "G" has a length which is somewhat shorter than the distance between the surfaces 10a, 10b.

The length of the incandescent filament and the chosen distance between the surfaces 10a, 10b is significant to the present invention.

Figure 8:
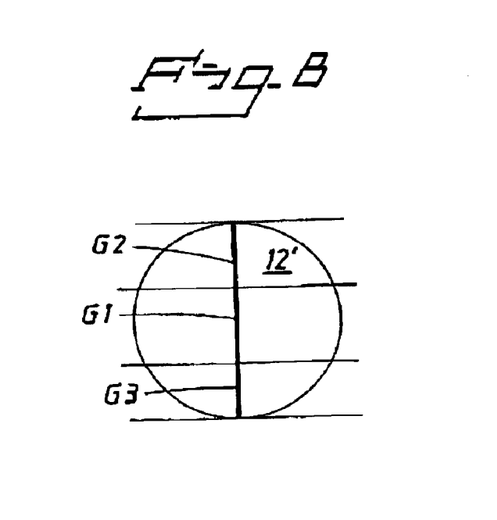
FIG. 8 is a detector view of the incandescent filament at a chosen, optimised cavity height.

FIG. 8 shows a detector view or a detector field of view 12' at a chosen, optimized cavity height between the surfaces 10a, 10b.

It will be seen from this that the directly-acting light bundle G1 emitted by the incandescent filament "G" is centered in respect of the field of view 12' of the detector 12, and that the light bundles G2, G3 reflected by the surfaces 10a, 10b are located immediately above and immediately beneath the light bundle G1, therewith enabling optimized light intensity to be obtained.

Figure 9:
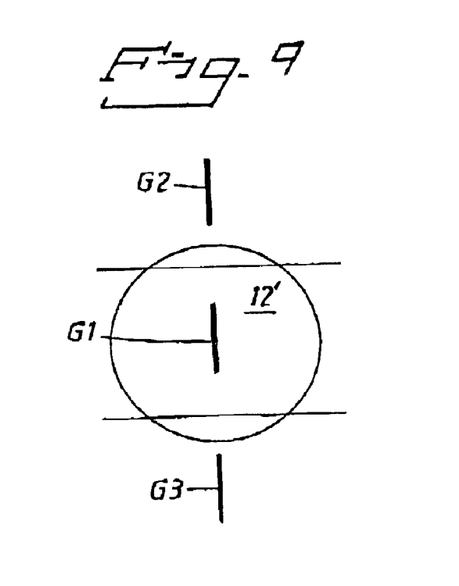
FIG. 9 is a detector view of the incandescent filament in respect of a chosen excessively extensive cavity height.

As will be evident from FIG. 9, the reflected light bundles G2 and G3 will lie outside the field of view 12' when said distance is excessively large.

In this regard, it lies within the scope of the invention to take measures such that in respect of the surfaces 10a, 10b the reflected light bundles G2 and G3 will be slightly laterally-related to the light bundle G1 within said field of view.

It will be apparent from this that by the expression that the distance between the light-reflecting surfaces 10a, 10b shall be chosen to correspond at least essentially to the actual length of the incandescent filament will also include a filament length that is slightly shorter (or greater) than said distance.

Although the exemplifying embodiment has been described with reference to an application for determining carbon dioxide contents of a gas, the gas cell can also be used for other applications.

It will be understood that the invention is not restricted to the aforedescribed and illustrated exemplifying embodiments thereof and that modifications can be made within the scope of the inventive concept as disclosed in the accompanying claims.

What is claimed is:

1. A gas cell comprising
a body having a cavity therein adapted for a chosen gas volume, a partially elliptical surface forming a reflector for a light source, the partially elliptical surface being comprised of two partially elliptical mirror surfaces, each partially elliptical mirror surface having an end part away from the other of the partially elliptical mirror surfaces, and the partially elliptical surface having a first focal point and a second focal point spaced from the first focal point;
a light source at the first focal point; the light source including an incandescent filament with a length;
two other cavity-defining and gas-conducting surfaces each extending respectively from one of the end-parts of the mirror surfaces;
a light-bundle receiving unit at the second focal point of the partially elliptical surface;
the cavity is delimited spaced apart parallel surfaces defining the cavity and meeting the partially elliptical mirror surfaces and the other cavity defining surfaces, wherein the distance between the spaced apart parallel surfaces corresponds essentially to the length of the incandescent filament in the light source.

2. A gas cell according to claim 1, wherein the two further gas-conducting surfaces are directly connected at the end-parts of the mirror surfaces.

3. A gas cell according to claim 1, wherein the elliptical shape of the mirror surfaces has a major axis and a minor axis, and the ratio between the major axis and the minor axis is in the range of 4:1 to 2:1.

4. A gas cell according to claim 1, further comprising a first plate including a first recess which is a first holder for the light source, and a second recess which is a second holder for the light-bundle receiving unit; and the cavity is formed in the first plate between the holders.

5. A gas cell according to claim 4, further comprising a second plate and a third plate operable to hold together the first plate and at least one sheet; and the second plate includes gas supply and gas discharge openings.

6. A gas cell according to claim 4, further comprising a second and a third plate adapted to hold together the first plate and at least one sheet; and the second plate includes gas supply and gas discharge openings.

7. A gas cell according to claim 1, further comprising a sheet applied to the plate, and the sheet includes a gas supply recess or opening and a gas discharge recess or opening.

8. A gas cell according to claim 7, further comprising a second and a third plate adapted to hold together the plate and at least one sheet; and the second plate includes gas supply and gas discharge openings.

9. A gas cell according to claim 1, further comprising an optical measurement path having a length of from 4 to 20 mm between the light source and the light-bundle receiving unit via the partially elliptical mirror surfaces.

10. A gas cell according to claim 1, wherein the cavity has a volumetric capacity of from 30 ml to 100 $\mu$l.

11. A gas cell according to claim 1, wherein a carbon dioxide containing gas to be analyzed travels in the cavity between the gas supply and discharge openings at a speed adapted to enable the gas to be replaced or exchanged from 1 to 50 times per second.

12. A gas cell according to claim 1, wherein the parallel surfaces are planar.

13. A gas cell according to claim 1, wherein the cavity has a gas supply opening or recess and a gas discharge opening or recess, and a pump for moving gas from the supply to the discharge the openings or recesses.

14. A gas cell according to claim 13, wherein the cavity between the gas supply and discharge openings is adapted to enable the gas to be exchanged or replaced 5 to 10 times per second.

15. A gas cell according to claim 1, wherein the cavity has a volumetric capacity of from 40 and 60 $\mu$l.

16. A gas cell according to claim 1, wherein the gas conducting surfaces are light absorbent.

* * * * *